(12) United States Patent
Shen et al.

(10) Patent No.: US 12,130,277 B2
(45) Date of Patent: Oct. 29, 2024

(54) METHOD AND SYSTEM OF PREDICTING FABRIC FEATURE

(71) Applicant: TAIWAN TEXTILE RESEARCH INSTITUTE, New Taipei (TW)

(72) Inventors: Pei-Te Shen, New Taipei (TW); Hung-Yu Lin, New Taipei (TW); Chin-Lun Chu, New Taipei (TW); Yu-Sian Ciou, New Taipei (TW); Tzu-Yu Chiu, New Taipei (TW)

(73) Assignee: TAIWAN TEXTILE RESEARCH INSTITUTE, New Taipei (TW)

( * ) Notice: Subject to any disclaimer, the term of this patent is extended or adjusted under 35 U.S.C. 154(b) by 173 days.

(21) Appl. No.: 17/732,645

(22) Filed: Apr. 29, 2022

(65) Prior Publication Data
US 2023/0333080 A1    Oct. 19, 2023

(30) Foreign Application Priority Data
Apr. 18, 2022   (TW) .................................. 111114724

(51) Int. Cl.
*G01N 33/36* (2006.01)
(52) U.S. Cl.
CPC .................................. *G01N 33/367* (2013.01)
(58) Field of Classification Search
CPC ............................. G01N 33/36; G01N 33/367
See application file for complete search history.

(56) References Cited

U.S. PATENT DOCUMENTS

| 2013/0325398 | A1* | 12/2013 | Nakagawa | G01N 19/02 |
| | | | | 702/170 |
| 2019/0259192 | A1 | 8/2019 | Ebrahimi et al. | |
| 2022/0391547 | A1* | 12/2022 | Bhatnagar | D04B 37/02 |

FOREIGN PATENT DOCUMENTS

| CN | 106909763 A | 6/2017 |
| CN | 108304351 A | 7/2018 |
| CN | 111177929 A | 5/2020 |

OTHER PUBLICATIONS

Cao, Jian-da et al., Regression analysis of the subjective assessment of cotton fabric handle, Journal of Textile Research, vol. 27, No. 1, Jan. 2006, 72-74.

Lai, Sang-Song, The Objective Evaluation Model of the Total Handle Value of Fabrics, Journal of Technology, vol. 16, No. 1, 2001, pp. 139-147.

\* cited by examiner

*Primary Examiner* — Nathaniel J Kolb
(74) *Attorney, Agent, or Firm* — McClure, Qualey & Rodack, LLP

(57) ABSTRACT

A method of predicting fabric features is disclosed herein, and the method includes following operations. Inputting first fabric information of a first fabric. Generating first fabric feature values of the first fabric. Performing a first calculation on the first fabric information and the first fabric feature values. Generating feature parameters and first predicted feature values of the first fabric by the first calculation. Inputting second fabric information of a second fabric. Generating second fabric feature values of the second fabric according to the second fabric information and the feature parameters. A system of predicting fabric features is also disclosed herein.

19 Claims, 4 Drawing Sheets

METHOD AND SYSTEM OF PREDICTING FABRIC FEATURE

CROSS-REFERENCE TO RELATED APPLICATION

This application claims priority to Taiwan Application Serial Number 111114724, filed Apr. 18, 2022, which is herein incorporated by reference in its entirety.

BACKGROUND

Technical Field

The present disclosure relates to a technology of predicting fabric features. More particularly, the present disclosure relates to a method and a system of predicting fabric features.

Description of Related Art

A fabric touch tester may be configured for measuring features of fabrics. However, performing measurements on every fabric consumes large amount of time and cost. Thus, techniques associated with the development for overcoming problems described above are important issues in the field.

SUMMARY

The present disclosure provides a method of predicting fabric features, and the method includes following operations. Inputting first fabric information of a first fabric. Generating first fabric feature values of the first fabric. Performing a first calculation on the first fabric information and the first fabric feature values. Generating feature parameters and first predicted feature values of the first fabric by the first calculation. Inputting second fabric information of a second fabric. Generating second fabric feature values of the second fabric according to the second fabric information and the feature parameters.

The present disclosure provides a system of predicting fabric features, and the system includes a fabric touch tester, a memory, and a processor. The fabric touch tester is configured to measure first fabric feature values of a first fabric. The memory is configured to store first fabric information of the first fabric. The processor is configured to generate feature parameters according to the first fabric information and the first fabric feature values, and configured to generate second predicted feature values of a second fabric according to second fabric information of the second fabric and the feature parameters.

The present disclosure provides a system of predicting fabric features, and the system includes a fabric touch tester, a memory, and a processor. The fabric touch tester is configured to measure first fabric feature values of a first fabric. The memory is configured to store second fabric information of a second fabric. The processor is configured to perform a first calculation on the first fabric information and the first fabric feature values, configured to generate feature parameters and first predicted feature values of the first fabric by the first calculation, and configured to generate second predicted feature values of the second fabric according to second fabric information of the second fabric and the feature parameters.

It is to be understood that both the foregoing general description and the following detailed description are by examples, and are intended to provide further explanation of the disclosure as claimed.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
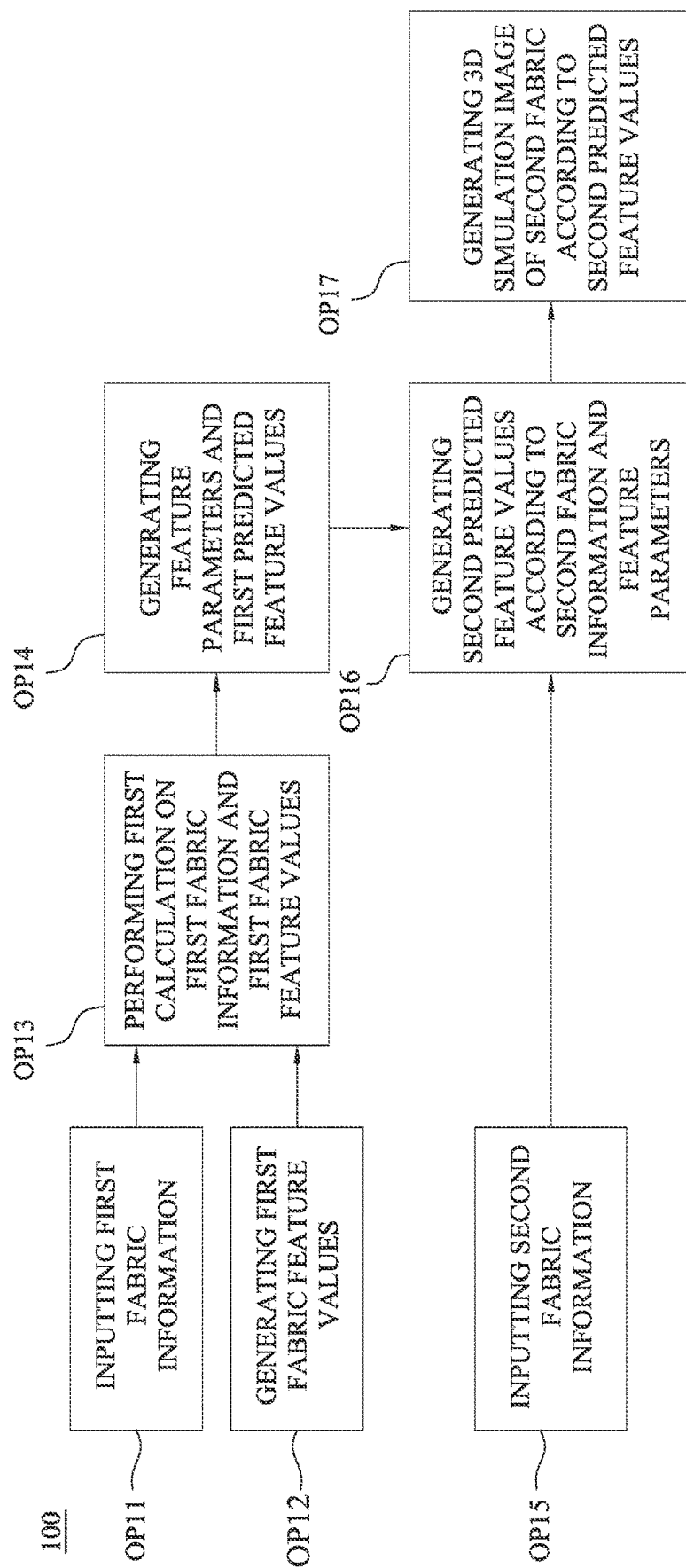
FIG. 1 is a flowchart diagram of a method of predicting fabric features illustrated according to one embodiment of the present disclosure.

In the present disclosure, when an element is referred to as "connected" or "coupled", it may mean "electrically connected" or "electrically coupled". "Connected" or "coupled" can also be used to indicate that two or more components operate or interact with each other. In addition, although the terms "first", "second", and the like are used in the present disclosure to describe different elements, the terms are used only to distinguish the elements or operations described in the same technical terms. The use of the term is not intended to be a limitation of the present disclosure.

Unless otherwise defined, all terms (including technical and scientific terms) used in the present disclosure have the same meaning as commonly understood by the ordinary skilled person to which the concept of the present invention belongs. It will be further understood that terms (such as those defined in commonly used dictionaries) should be interpreted as having a meaning consistent with its meaning in the related technology and/or the context of this specification and not it should be interpreted in an idealized or overly formal sense, unless it is clearly defined as such in this article.

The terms used in the present disclosure are only used for the purpose of describing specific embodiments and are not intended to limit the embodiments. As used in the present disclosure, the singular forms "a", "one" and "the" are also intended to include plural forms, unless the context clearly indicates otherwise. It will be further understood that when used in this specification, the terms "comprises (comprising)" and/or "includes (including)" designate the existence of stated features, steps, operations, elements and/or components, but the existence or addition of one or more other features, steps, operations, elements, components, and/or groups thereof are not excluded.

Hereinafter multiple embodiments of the present disclosure will be disclosed with schema, as clearly stated, the details in many practices it will be explained in the following description. It should be appreciated, however, that the details in these practices is not applied to limit the present disclosure. Also, it is to say, in some embodiments of the present disclosure, the details in these practices are non-essential. In addition, for the sake of simplifying schema, some known usual structures and element in the drawings by a manner of simply illustrating for it.

FIG. 1 is a flowchart diagram of a method 100 of predicting fabric features illustrated according to one embodiment of the present disclosure. Referring to FIG. 1, the method 100 includes operations OP11-OP17.

At the operation OP11, inputting first fabric information of a first fabric. In some embodiments, the first fabric information includes fabric ingredients, a fabric weight, and a fabric texture of the first fabric. In some embodiments, the first fabric information further includes a width, drape coefficients, elasticity coefficients, woven parameters, dyeing parameters, finishing parameters, layering information, functions and/or fit types of the first fabric.

Figure 4:
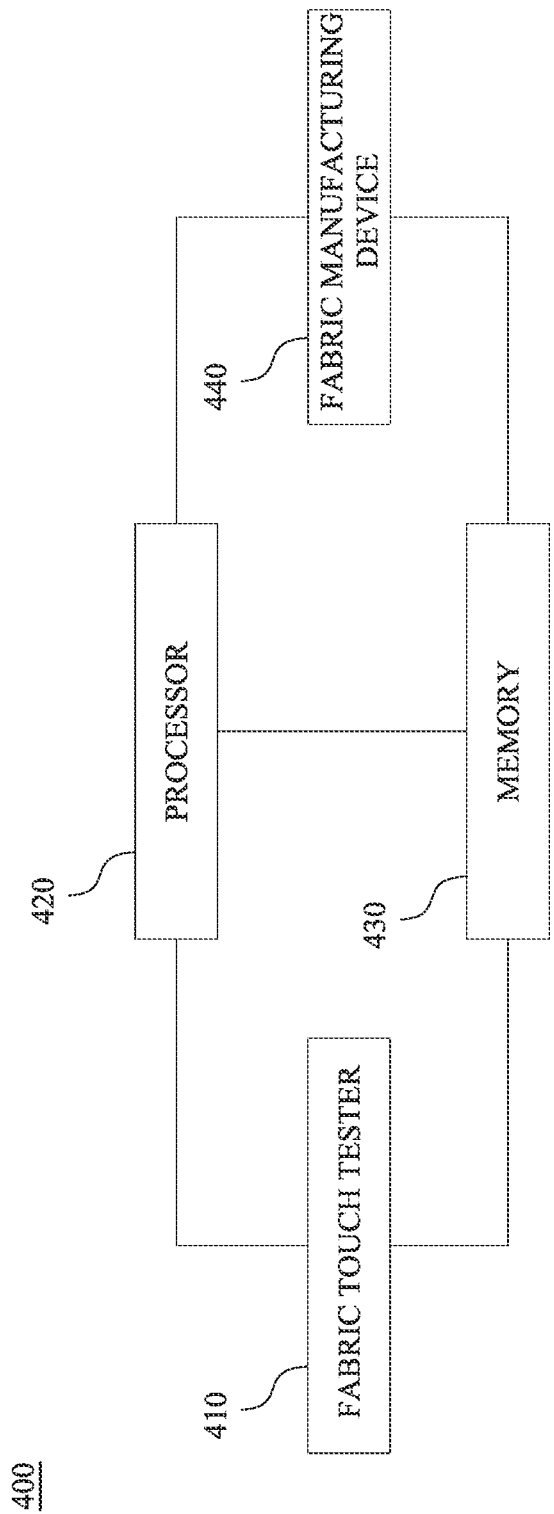
FIG. 4 is a schematic diagram of a system of predicting fabric features illustrated according to one embodiment of the present disclosure.

At the operation OP12, generating first fabric feature values of the first fabric. In some embodiments, a fabric touch tester 410 shown in FIG. 4 is configured to perform measurements on the first fabric, to generate the first fabric feature values. In some embodiments, the first fabric feature values include an actual smoothness, an actual softness, and actual warmth of the first fabric.

At the operation OP13, performing a first calculation on the first fabric information and the first fabric feature values. In some embodiments, a processor 420 shown in FIG. 4 is configured to perform the first calculation on the first fabric information and the first fabric feature values. In some embodiments, the first calculation includes a linear regression analysis, a principal components analysis, and/or a k-means algorithm. For example, the first calculation uses the linear regression analysis model having a function of the first fabric information for predicting fabric features to fit the first fabric feature values.

At the operation OP14, generating multiple feature parameters and multiple first predicted feature values of the first fabric by the first calculation. In some embodiments, the first predicted feature values include a first predicted smoothness, a first predicted softness and first predicted warmth of the first fabric.

At the operation OP15, inputting second fabric information of a second fabric. In some embodiments, the second fabric information includes fabric ingredients, a fabric weight, and a fabric texture of the second fabric. In some embodiments, the second fabric information further includes a width, drape coefficients, elasticity coefficients, woven parameters, dyeing parameters, finishing parameters, layering information, functions and/or fit types of the second fabric.

At the operation OP16, generating multiple second predicted feature values of the second fabric according to the second fabric information and the feature parameters. In some embodiments, the second predicted feature values include a second predicted smoothness, a second predicted softness, and second predicted warmth of the second fabric. For example, the second predicted softness may be generated by calculation of the equation (1): the second predicted softness=$C1+X1\times Z1+X2\times Z2+X3\times Z3$ . . . equation (1), in which C1 is a constant term, X1-X3 are coefficients, and Z1-Z3 are the feature parameters generated by the operations OP14. As shown in the equation (1) above, the second predicted softness is linear dependent with each of the feature parameters Z1-Z3. In some embodiments, the second predicted softness and the second predicted warmth may be generated by similar equations.

At the operation OP17, generating a 3D simulation image of the second fabric according to the second predicted feature values of the second fabric.

Generally speaking, if someone wants to know fabric feature values of multiple fabrics, a fabric touch tester is required for performing measurements on each of the fabrics to obtain the fabric feature values thereof. The approach consumes a large amount of time and has a higher cost.

Comparing to above approach, the present disclosure can generate the feature parameters by the operations OP11-OP14, and obtain the second predicted feature values of the second fabric according to the feature parameters. Alternatively stated, the second predicted feature values of the second fabric can be obtained without using the fabric touch tester. In this way, the method provided in the present disclosure can reduce time and cost needed of user to measure the second fabric, so that the information of the second fabric can be obtained with higher efficiency. In some embodiments, the users described above may be fabric manufacturers, information suppliers, or ordinary consumers.

Figure 2:
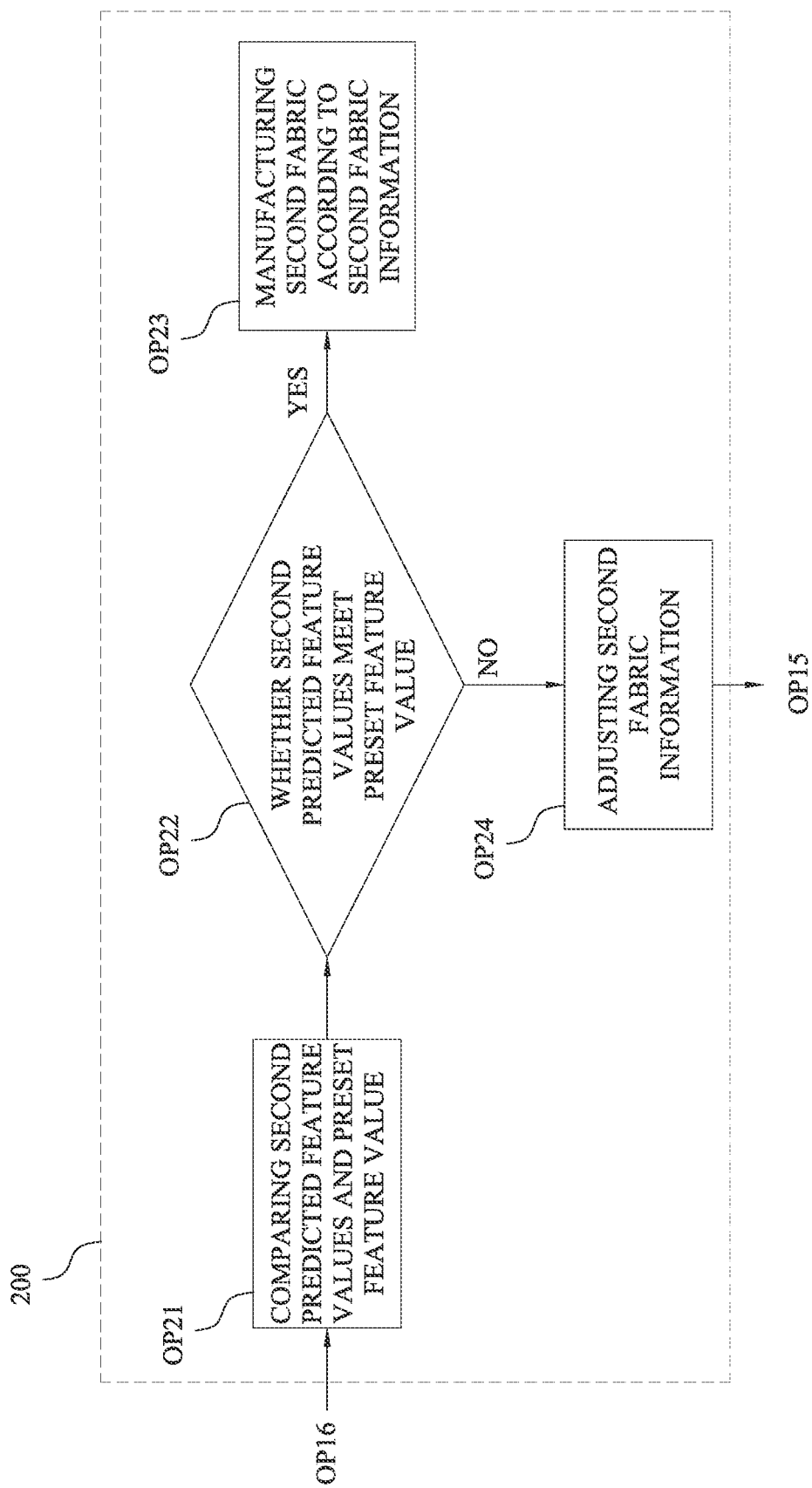
FIG. 2 is a flowchart diagram of a method of predicting fabric features illustrated according to one embodiment of the present disclosure.

FIG. 2 is a flowchart diagram of a method 200 of predicting fabric features illustrated according to one embodiment of the present disclosure. Referring to FIG. 2, the method 200 includes operations OP21-OP24. In some embodiments, the method 200 is performed after the operation OP16 shown in FIG. 1.

At the operation OP21, comparing the second predicted feature values and at least one preset feature value. In some embodiments, the memory 430 shown in FIG. 4 is configured to store the at least one preset feature value. In some embodiments, the at least one preset feature value includes a preset smoothness, a preset softness and a preset warmth.

At the operation OP22, determining whether the second predicted feature values meet the at least one preset feature value. For example, determining whether the second predicted smoothness is larger than the preset smoothness; determining whether the second predicted softness is larger than the preset softness; and/or determining whether the second predicted warmth is larger than the preset warmth.

When the operation OP22 determines that the second predicted feature values meet the at least one preset feature value, the operation OP23 is performed. At the operation OP23, manufacturing the second fabric according to the second fabric information.

When the operation OP22 determines that the second predicted feature values do not meet the at least one preset feature value, the operation OP24 is performed. At the operation OP24, adjusting the second fabric information. In some embodiments, after the operation OP24, the adjusted second fabric information is used to perform the operations OP15 and OP16 to generate the second predicted feature values corresponding to the adjusted second fabric information. Then, the method 200 is performed again. In some embodiments, the operations OP15, OP16, OP21, OP22 and OP24 are performed repeatedly until the second predicted feature values meet the at least one preset feature value. As a result, the user can find the second fabric which meets usage requirements (that is, the preset feature values).

Figure 3:
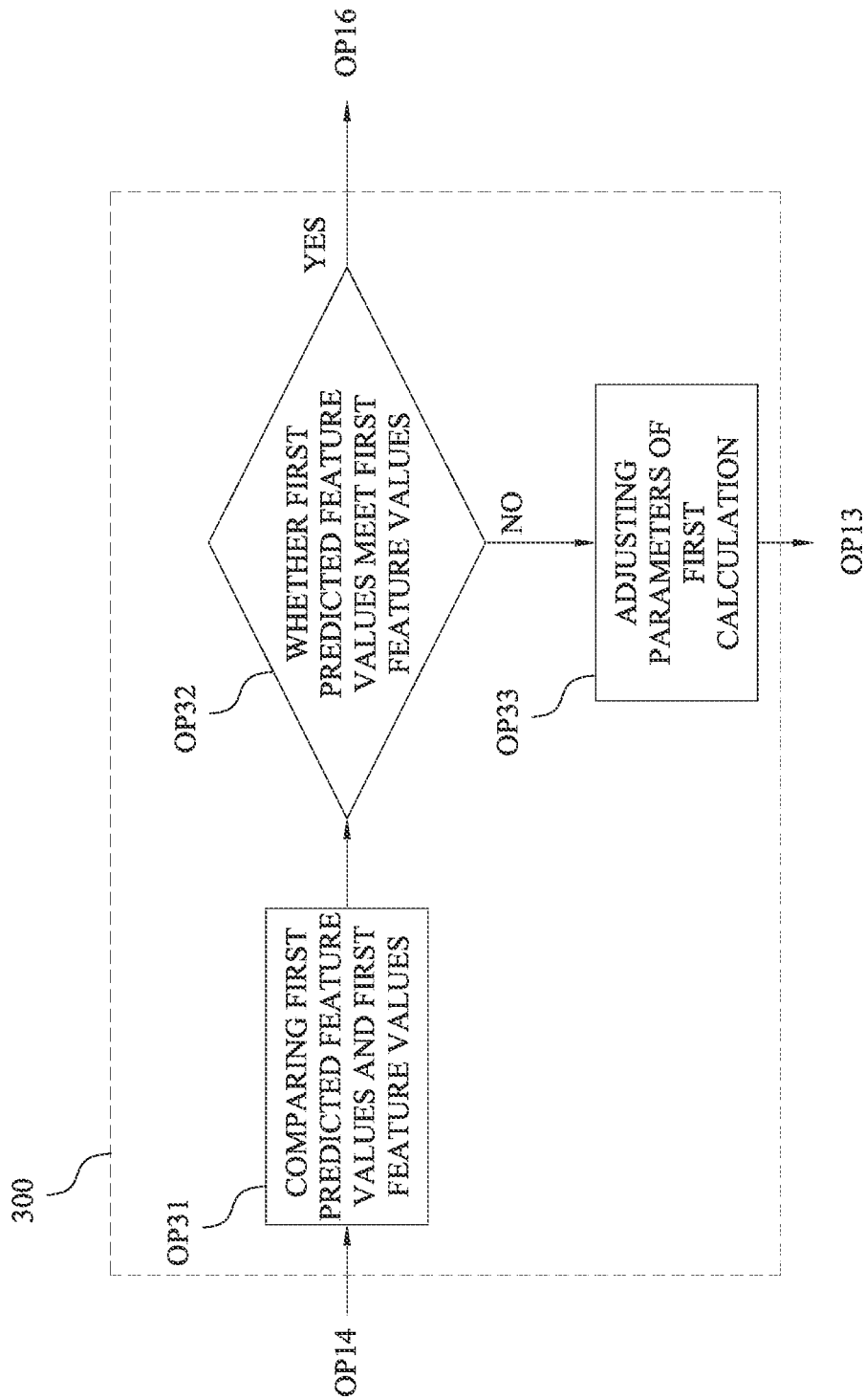
FIG. 3 is a flowchart diagram of a method of predicting fabric features illustrated according to one embodiment of the present disclosure.

FIG. 3 is a flowchart diagram of a method 300 of predicting fabric features illustrated according to one embodiment of the present disclosure. Referring to FIG. 3, the method 300 includes operations OP31-OP33. In some embodiments, the method 300 is performed between the operations OP14 and OP16 shown in FIG. 1.

At the operation OP31, comparing the first predicted feature values and the first feature values.

At the operation OP32, determining whether the first predicted feature values meet the first feature values. When the first predicted feature values meet the first feature values, the operation OP16 is performed. When the first predicted feature values do not meet the first feature values, the operation OP33 is performed.

At the operation OP33, adjusting parameters of the first calculation. For example, adjusting the constant term C1 and/or the coefficients X1-X3 shown in the equation described above.

After the operation OP33 is performed, the operations OP13 and OP14 are performed again with the adjusted parameters, to generate the first predicted feature values corresponding to the adjusted parameters. In some embodiments, the operations OP13, OP14, OP31, OP32 and OP33 are performed repeatedly until the first calculation can generate the first predicted feature values which meet the first feature values.

FIG. 4 is a schematic diagram of a system 400 of predicting fabric features illustrated according to one embodiment of the present disclosure. Referring to FIG. 4, the system 400 includes a fabric touch tester 410, a processor 420, a memory 430, and a fabric manufacturing device 440. In some embodiments, the fabric touch tester 410 is coupled to the processor 420 and the memory 430, the fabric manufacturing device 440 is coupled to the processor 420 and the memory 430, and the processor 420 and the memory 430 are coupled to each other.

In some embodiments, the fabric touch tester 410 is configured to measure the first fabric feature values of the first fabric. The memory 430 is configured to store the first fabric information of the first fabric. The processor 420 is configured to generate the feature parameters according to the first fabric information and the first fabric feature values, and configured to generate the second predicted feature values of the second fabric according to the second fabric information of the second fabric and the feature parameters.

In some embodiments, the first fabric information includes first fabric ingredients, a first fabric weight, and a first fabric texture of the first fabric, the second fabric information includes second fabric ingredients, a second fabric weight, and a second fabric texture of the second fabric, the first fabric feature values include the actual smoothness, the actual softness, and the actual warmth of the first fabric, and the second predicted feature values include the second predicted smoothness, the second predicted softness, and the second predicted warmth of the second fabric.

In some embodiments, at least one of the second predicted smoothness, the second predicted softness, and the second predicted warmth is linear dependent with each of the feature parameters.

In some embodiments, the fabric manufacturing device 440 is configured to manufacture the second fabric according to the second fabric information when the second predicted feature values meet the at least one preset feature value. In some embodiments, the processor 420 is further configured to adjust the second fabric information when the second predicted feature values do not meet the at least one preset feature value.

Referring to FIG. 1 to FIG. 4, each of the operations OP11-OP17, OP21-OP24, and OP31-OP33 may be performed by the system 400. In some embodiments, the processor 420 is configured to perform parts or all of the operations OP11, OP13-OP17, OP21, OP22, OP24, and OP31-OP33. In some embodiments, the fabric touch tester 410 is configured to perform the operation OP12. In some embodiments, the fabric manufacturing device 440 is configured to perform the operation OP23. In some embodiments, the memory 430 is configured to store parts or all of the first fabric information, the first fabric feature values, the second fabric information, the feature parameters, the first predicted feature values, the second predicted feature values, and the at least one preset feature value.

In summary, the methods 100, 200, and/or 300 performed by the system 400 can predict the second fabric feature values from the second fabric information directly but without measuring the second fabric. Comparing with traditional approaches, embodiments of the present disclosure can largely reduce the time and the cost for measuring the second fabric.

Although the present disclosure has been described in considerable detail with reference to certain embodiments thereof, other embodiments are possible. Therefore, the spirit and scope of the appended claims should not be limited to the description of the embodiments contained in the present disclosure.

It will be apparent to those skilled in the art that various modifications and variations can be made to the structure of the present disclosure without departing from the scope or spirit of the disclosure. In view of the foregoing, it is intended that the present disclosure cover modifications and variations of the present disclosure provided they fall within the scope of the following claims.

What is claimed is:

1. A method of predicting fabric features, comprising:
inputting first fabric physical information of a first fabric that has been produced;
performing measurements of first fabric feature values of the first fabric by a fabric touch tester;
performing a first calculation on the first fabric physical information and the first fabric feature values;
generating feature parameters and first predicted feature values of the first fabric by the first calculation, wherein the first predicted feature values comprise a first predicted smoothness, a first predicted softness, and first predicted warmth of the first fabric;
inputting second fabric desired information of a second fabric that has not been produced; and
generating second predicted feature values of the second fabric according to the second fabric desired information and the feature parameters of the first fabric,
wherein the second predicted feature values comprise a second predicted softness of the second fabric, the second predicted softness is equal to $C1+X1\times Z1+X2\times Z2+X3\times Z3$, C1 is a constant term, X1, X2 and X3 are coefficients, and Z1, Z2 and Z3 are the feature parameters.

2. The method of claim 1, wherein the first fabric physical information comprises first fabric ingredients, a first fabric weight, and a first fabric texture of the first fabric.

3. The method of claim 2, wherein the second fabric desired information comprises second fabric ingredients, a second fabric weight, and a second fabric texture of the second fabric.

4. The method of claim 1, wherein performing the measurements of the first fabric feature values of the first fabric by the fabric touch tester comprises:
performing the measurements on the first fabric by the fabric touch tester, to generate an actual smoothness, an actual softness, and actual warmth of the first fabric,
wherein the first fabric feature values include the actual smoothness, the actual softness, and the actual warmth of the first fabric.

5. The method of claim 1, wherein the second predicted feature values further comprise a second predicted smoothness, and second predicted warmth of the second fabric.

6. The method of claim 1, further comprising:
comparing the second predicted feature values and at least one preset feature value; and
when the second predicted feature values meet the at least one preset feature value, manufacturing the second fabric according to the second fabric desired information.

7. The method of claim 6, further comprising:
when the second predicted feature values do not meet the at least one preset feature value, adjusting the second fabric desired information.

8. The method of claim 7, further comprising:
after the second fabric desired information is adjusted, generating the second predicted feature values corresponding to the adjusted second fabric desired information.

9. The method of claim 1, further comprising:
comparing the first predicted feature values and the first feature values; and
when the first predicted feature values meet the first feature values, generating the second predicted feature values according to the second fabric desired information and the feature parameters of the first fabric.

10. The method of claim 9, further comprising:
when the first predicted feature values do not meet the first feature values, adjusting parameters of the first calculation.

11. The method of claim 1, wherein the first fabric physical information comprises a width, drape coefficients, elasticity coefficients, woven parameters, dyeing parameters, finishing parameters, layering information, functions or fit types of the first fabric.

12. The method of claim 1, wherein the second fabric desired information comprises a width, drape coefficients, elasticity coefficients, woven parameters, dyeing parameters, finishing parameters, layering information, functions or fit types of the second fabric.

13. A system of predicting fabric features, comprising:
a fabric touch tester configured to measure first fabric feature values of a first fabric that has been produced;
a memory configured to store first fabric physical information of the first fabric; and
a processor configured to generate feature parameters according to the first fabric physical information and the first fabric feature values, and configured to generate second predicted feature values of a second fabric that has not been produced according to second fabric desired information of the second fabric and the feature parameters of the first fabric,
wherein the second predicted feature values comprise a second predicted softness of the second fabric, the second predicted softness is equal to $C1+X1 \times Z1+X2 \times Z2+X3 \times Z3$, C1 is a constant term, X1, X2 and X3 are coefficients, and Z1, Z2 and Z3 are the feature parameters.

14. The system of claim 13, wherein
the first fabric physical information comprises first fabric ingredients, a first fabric weight, and a first fabric texture of the first fabric,
the second fabric desired information comprises second fabric ingredients, a second fabric weight, and a second fabric texture of the second fabric,
the first fabric feature values include an actual smoothness, an actual softness, and actual warmth of the first fabric, and
the second predicted feature values include a second predicted smoothness, the second predicted softness, and second predicted warmth of the second fabric.

15. The system of claim 14, wherein at least one of the second predicted smoothness, the second predicted softness, and the second predicted warmth is linear dependent with each of the feature parameters.

16. The system of claim 14, further comprising:
a fabric manufacturing device configured to manufacture the second fabric according to the second fabric desired information when the second predicted feature values meet at least one preset feature value,
wherein the processor is further configured to adjust the second fabric desired information when the second predicted feature values do not meet the at least one preset feature value.

17. A system of predicting fabric features, comprising:
a fabric touch tester configured to measure first fabric feature values of a first fabric that has been produced;
a memory configured to store first fabric physical information of the first fabric and second fabric desired information of a second fabric that has not been produced; and
a processor configured to perform a first calculation on the first fabric physical information and the first fabric feature values, configured to generate feature parameters of the first fabric and first predicted feature values of the first fabric by the first calculation, and configured to generate second predicted feature values of the second fabric according to the second fabric desired information of the second fabric and the feature parameters of the first fabric, wherein the first predicted feature values comprise a first predicted smoothness, a first predicted softness, and first predicted warmth of the first fabric
wherein the second predicted feature values comprise a second predicted softness of the second fabric, the second predicted softness is equal to $C1+X1 \times Z1+X2 \times Z2+X3 \times Z3$, C1 is a constant term, X1, X2 and X3 are coefficients, and Z1, Z2 and Z3 are the feature parameters.

18. The system of claim 17, wherein the processor is further configured to adjust parameters of the first calculation when the first predicted feature values do not meet the first feature values.

19. The system of claim 17, wherein the processor is further configured to adjust the second fabric desired information when the second predicted feature values do not meet at least one preset feature value, and configured to generate the second predicted feature values corresponding to the adjusted second fabric desired information.

* * * * *